United States Patent [19]

Erpenbach et al.

[11] 3,985,800

[45] Oct. 12, 1976

[54] PROCESS FOR THE MANUFACTURE OF ACRYLIC ACID

[75] Inventors: Heinz Erpenbach, Surth; Klaus Gehrmann, Hurth-Knapsack; Winfried Lork, Erftsdadt Friesheim; Peter Prinz, Hurth-Burbach, all of Germany

[73] Assignee: Hoechst Aktiengesellschaft, Frankfurt/Main, Germany

[22] Filed: Aug. 31, 1973

[21] Appl. No.: 393,347

[30] Foreign Application Priority Data

Sept. 5, 1972 Germany............................ 2243584

[52] U.S. Cl............................... 260/530 N; 252/470
[51] Int. Cl.² ...............................................C07C; 51/32
[58] Field of Search................................. 260/530 N

[56] References Cited

UNITED STATES PATENTS

| | | | |
|---|---|---|---|
| 3,322,693 | 5/1967 | Bethell et al................ | 260/530 N X |
| 3,365,489 | 1/1968 | Bethell et al................ | 260/530 N |
| 3,415,760 | 12/1968 | Hadeley et al................ | 260/530 N |
| 3,578,707 | 5/1971 | Bethell et al................ | 260/530 N |

FOREIGN PATENTS OR APPLICATIONS

| | | | |
|---|---|---|---|
| 915,799 | 1/1963 | United Kingdom................ | 260/530 N |
| 915,800 | 1/1963 | United Kingdom................ | 260/530 N |
| 878,802 | 10/1961 | United Kingdom................ | 260/530 N |

OTHER PUBLICATIONS

Mitchell—editor—Chemistry Uses of Molybdenum—proceedings of conference held at University of Reading, England, Sept. 17-21, 1973.

Haber—Bulletin de L'Andemie Polonaise des Sciences, vol. XIX, No. 8, 1971, pp. 497-500.

*Primary Examiner*—Vivian Garner
*Attorney, Agent, or Firm*—Connolly and Hutz

[57] ABSTRACT

Production of acrylic acid by reacting acrolein with molecular oxygen in the presence of steam and, if desired, inert gases at elevated temperature in contact with a fixed bed of cobalt molybdate catalyst prepared by precipitating cobalt molybdate from the combined aqueous solutions of a cobalt salt, of a molybdenum compound and of ammonia at a temperature of about 60°C and at a pH of at most 7; filtering off, washing and drying the precipitate at a temperature of at least 100°C; heating the dry cobalt molybdate for several hours at elevated temperatures, grinding and transforming it into shapes; and sintering the cobalt molybdate shapes for several hours. The acrylic acid is more particularly produced in contact with a catalyst prepared by combining the aqueous solution of the cobalt salt with that of the molybdenum compound in the atomic ratio of Co:Mo of about 1.05:1; establishing in the combined solutions a pH between 3.8 and 6.0; drying the precipitate at 110°–170°C; heating the dry cobalt molybdate to temperatures between 250° and 550°C; and sintering the cobalt molybdate shapes at temperatures between 500° and 700°C so as to obtain a cobalt molybdate catalyst having an inner surface area between 4 and 8 square meters/g and a volume of pores between 0.1 and 0.2 milliliters/g.

5 Claims, No Drawings

PROCESS FOR THE MANUFACTURE OF ACRYLIC ACID

The production of acrylic acid by reacting acrolein with molecular oxygen in the presence of steam and, if desired, one or more inert gases at elevated temperature and in contact with a fixed bed cobalt molybdate catalyst has already been described in German published Specification "Auslegeschrift" 1 417 670. In this process, use is made of a catalyst which is prepared by precipitating cobalt molybdate from the combined aqueous solutions of a cobalt salt, of a molybdenum compound and of ammonia at a temperature of about 60°C and at a pH of at most 7; filtering off, washing and drying the precipitate at a temperature of at least 100°C; heating the dry cobalt molybdate for several hours at elevated temperatures; grinding and transforming it into shapes and sintering the cobalt molybdate shapes for several hours. Similar processes have been disclosed in German published Specification "Offenlegungsschrift" 1 418 750 and in German published Specification "Auslegeschrift" 1 184 326. This latter Specification is noted to indicate in column 3, line 14, a surface area between 16 and 17 square meters/g for the catalyst.

The processes used heretofore for making acrylic acid in contact with cobalt molybdate catalysts have considerable disadvantages. More particularly the cobalt molybdate catalysts have been found to either combine satisfactory hardness with minor selectivity or to combine satisfactory selectivity with poor resistance to abrasion. It should be added that the catalysts made by prior art methods rapidly undergo a decrease in activity, are difficultly reproducible and are irregularly selective.

The present invention now provides a process for making acrylic acid in contact with cobalt molybdate catalysts, which combine good abrasion resistance with good selectivity and long service life, which process comprises producing the acrylic acid in contact with a catalyst prepared by combining the aqueous solution of the cobalt salt with that of the molybdenum compound in the atomic ratio of Co:Mo of about 1.05:1; establishing in the combined solutions a pH between 3.8 and 6.0; drying the precipitate at 110°–170°C; heating the dry cobalt molybdate to temperatures between 250° and 550°C; and sintering the shapes of cobalt molybdate at temperatures between 500° and 700°C with the resultant formation of a cobalt molybdate catalyst having an inner surface area between 4 and 8 square meters/g and a volume of pores between 0.1 and 0.2 milliliters/g.

Further features of the process of the present invention, which can be used singly or in combination comprise making the catalyst by:

a. combining an aqueous solution of cobalt nitrate with an aqueous ammoniacal solution of ammonium molybdate;
b. adjusting the pH to a value between 4.0 and 4.4;
c. grinding the cobalt molybdate and then compressing it into pellets with the use of about 2–5 weight% of graphite as a pelleting auxiliary;
d. sintering the shapes of cobalt molybdate so as to establish an inner surface area between 5 and 7 square meters/g in the resulting cobalt molybdate catalyst.

The present process for making acrylic acid should preferably be effected at temperatures between 350° and 410°C and under pressures of 1–4 atmospheres absolute. The contact time may be selected between 0.5 and 5 seconds. Acrolein, oxygen, steam and balance gases ($N_2$, $CO_2$, CO, saturated hydrocarbons) should be used in a ratio by volume of about 1:(1–1.7):(1.7–4):(8–30), preferably 1:(1.3–1.5):(2–2.5):(12–20). These operational data do not form part of the present invention.

In the production of an active catalyst as described hereinabove, it is an important requirement for the catalyst to be precipitated from aqueous solutions containing Co and Mo in an atomic ratio of about 1.05:1. Using atomic ratios outside this range results in catalysts of impaired selectivity. In the processes first referred to hereinabove, use has been made of solutions containing Co and Mo in an atomic ratio of 1.00:1.00.

In accordance with this invention, it is also necessary for the precipitation to be effected exactly within the pH ranges between 3.8 and 6.0, preferably between 4.0 and 4.4, as this is critical for the structure, strength and reproducibility of the catalyst. The heat treatment, which should conveniently be effected over a period of 12–20 hours at 250° bis 550°C, prior to the pelleting and sintering steps, has been found to improve the selectivity and resistance to abrasion of the catalyst. After transformation into pellets, the catalyst should be sintered over a preferred period of 6–10 hours at 500°–700°C so as to establish an inner BET-surface area between 4 and 8 square meters/g, preferably between 5 and 7 square meters/g and a volume of pores between 0.1 and 0.2 milliliters/g. By establishing an inner surface area within these narrow limits, it is possible to produce catalysts which combine optimum selectivity with a long service life and with the necessary hardness. Larger surface areas actually increase the catalyst's activity (conversion of acrolein) but they reduce its hardness and selectivity. Smaller surface areas in turn cause inactivation of the catalyst. As will more clearly result particularly from comparative Examples 3 to 8 hereinafter, catalysts having less good overall properties were obtained in all those experiments which were carried out under conditions outside those specified in the present invention.

EXAMPLE 1

An ammoniacal solution of 384 g of ammonium heptamolybdate $(NH_4)_6Mo_7O_{24} \cdot 4 H_2O$ in 549 g of water was added to a solution of 665 g of cobalt nitrite $Co(NO_3)_2 \cdot 6 H_2O$ in 648 g of water, at 60°C and at a pH between 4.2 and 4.4. This resulted in the precipitation of cobalt molybdate. The solutions used contained Co and Mo in an atomic ratio of 1.05:1. The precipitate was filtered off, washed with water and dried at 150°C. The dry cobalt molybdate was subjected to thermal treatment over 16 hours at 500°C, ground, admixed with 2–5 weight% of graphite and compressed into pellets with the dimensions of 4×5 mm. The pellets so made were finally sintered for 8 hours at 600°C and then had an inner surface area of 5.8 square meters/g and a volume of pores of 0.15 milliliters/g.

200 milliliters of cobalt molybdate catalyst so produced were placed in a reactor 1 m long and 25 mm wide, which was heated by means of salt bath. At a salt bath temperature of 375°C, the catalyst was supplied, per hour, with 27 normal liters (S.T.P.) of acrolein, 42 normal liters of oxygen, 345 normal liters of nitrogen and 105 normal liters of steam. The products coming from the reactor were condensed and the acrylic acid obtained was analyzed. 41 g/hr of acrylic acid were obtained. The acrolein conversion rate and the acrylic acid yield or selectivity were determined along the following formula:

$$\text{Acrolein conversion rate (\%)} = \frac{\text{Mols of acrolein used} - \text{mols of acrolein recovered}}{\text{Mols of acrolein used}} \cdot 100$$

Acrylic acid yield or selectivity (%) = (Mols of acrylic acid · 100/Mols of acrolein converted).

The acrolein conversion rate was 53%, the selectivity was 89.5% and the catalyst performance was 205 grams of acrylic acid per liter of catalyst per hour.

EXAMPLE 2

The catalyst was the same as that used in Example 1, save that it was sintered for 7 hours at 600°C, had an inner surface area of 6.6 square meters/g and a volume of pores of 0.15 milliliters/g. 34 liters of the catalyst were placed in a reactor comprising 31 tubular structures 2.50 meters long and 25 mm wide. The reactor was heated by means of a salt bath.

At a salt bath temperature of 385°C, the catalyst was fed, per hour, with a mixture of 4.36 normal cubic meters of acrolein, 7.42 normal cubic meters of oxygen, 50 normal cubic meters of carbon monoxide/carbon dioxide and 10.9 normal cubic meters of steam. The resulting reaction products were water-washed and 7 480 g/hr of acrylic acid were isolated therefrom, unreacted acrolein being recycled to the reactor, together with recycle gas. The acrolein conversion rate was 58% and acrylic acid was obtained in a yield (selectivity) of 90.5%. The catalyst performance was 220 g of acrylic acid per liter of catalyst per hour. After 6 months of operation, the activity of the catalyst could not be found to have been impaired.

The following Examples 3 to 8 are given for the purpose of comparison.

EXAMPLE 3

An atomic ratio of Co:Mo exactly of 1:1 (prior art) was established in the solutions. The starting material, which was a solution of 634 g of cobalt nitrate in 648 g of water, was admixed at 60°C at a pH between 4.2 and 4.4 with an ammoniacal solution of 384 g of ammonium heptamolybdate in 549 g of water to effect precipitation. The precipitate was then treated in the manner described in Example 1.

The catalyst so made, which had a surface area of 6.5 square meters/g and a volume of pores of 0.17 milliliters/g, enabled the production of 40.5 g/hr of acrylic acid, for an acrolein conversion rate of 58%. This corresponded to a selectivity of merely 79% for a catalyst performance of 203 g of acrylic acid per liter of catalyst per hour.

EXAMPLE 4

The starting solutions contained Co and Mo in the atomic ratio of 1.1:1. Precipitation of the starting solution of 698 g of cobalt nitrate in 648 g of water was effected at 60°C at a pH between 4.2 and 4.4 with the use of an ammoniacal solution of 384 g of ammonium heptamolybdate in 549 g of water. The resulting precipitate was then treated under the conditions reported in Example 1. The catalyst so made, which had a surface area of 6.2 square meters/g and a volume of pores of 0.14 milliliters/g, produced 37 g/hr of acrylic acid, for an acrolein conversion rate of 54 %. This corresponded to a selectivity of merely 77.5%, for a catalyst performance of 185 g of acrylic acid per liter of catalyst per hour.

EXAMPLE 5

The procedure was the same as that described in Example 1, save that the ammoniacal solution of ammonium heptamolybdate was admixed with the quantity of ammonia necessary to effect precipitation at a pH higher than 6 up to 7. The catalyst, which was further treated in the manner described in Example 1, had a surface area of 6.7 square meters/g and a volume of pores of 0.18 milliliters/g. As compared with the catalyst made in accordance with this invention, it was substantially less resistant to abrasion. This was demonstrated by the fact that the catalyst pellets were found to have been decomposed after a few days of operation. The catalyst produced 39 g/hr of acrylic acid for an acrolein conversion rate of 61%. This corresponded to a selectivity of 72.2%, for a catalyst performance of 195 g of acrylic acid per liter of catalyst per hour.

EXAMPLE 6

The procedure was the same as that described in Example 1, save that the ammoniacal ammonium heptamolybdate solution was admixed with the quantity of ammonia necessary to ensure precipitation at a pH of 3.5. The resulting catalyst, which was further treated in the manner described in Example 1, had a surface area of 5.6 square meters/g, a volume of pores of 0.16 milliliters/g and a minor resistance to abrasion. The catalyst produced 32 g/hr of acrylic acid for an acrolein conversion rate of 46%. This corresponded to a selectivity of 78.6%, for a catalyst performance of 160 g of acrylic acid per liter of catalyst per hour.

EXAMPLE 7

The procedure was the same as that described in Example 1 save that the catalyst pellets were finally sintered over a period of merely 4 hrs at 600°C. This gave a catalyst which had a surface area of 9.6 square meters/g and a volume of pores of 0.25 milliliters/g. The catalyst so made had a mechanical strength lower than that of the catalysts made in Examples 1 and 2. The catalyst was tested in the manner described in Example 2 and found to produce 7 100 g/hr of acrylic acid for an acrolein conversion rate of 60%. This corresponded to a selectivity of 82.9%, for a catalyst performance of 209 g of acrylic acid per liter of catalyst per hour. It was necessary for the test to be interrupted after as short a period as 18 days, as the catalyst was found to have been decomposed.

EXAMPLE 8

The procedure was the same as that described in Example 1, save that the catalyst pellets were finally sintered for 12.5 hours at 600°C until the catalyst was found to have a surface area of 3.0 square meters/g and a volume of pores of 0.08 milliliters/g. Apart from its minor resistance to abrasion, the catalyst so made produced merely 14 g/hr of acrylic acid for an acrolein conversion rate of 28%, under the conditions reported in Example 1. This corresponded to a selectivity of 56.6%, for a catalyst performance of 70 g of acrylic acid per liter of catalyst per hour.

The results obtained in Examples 1 to 8 are summarized in the following Table indicating that merely the catalysts prepared in accordance with this invention (Examples 1 and 2) could be found to produce optimum results as regards selectivity for acrylic acid.

TABLE

| Example No. | Atomic ratio of Co : Mo in solutions | pH during precipitation | BET-surface area in sqm/g | Volume of pores in ml/g | Selectivity for acrylic acid in % | Catalyst performance (g acrylic acid per liter of catalyst per hour) |
|---|---|---|---|---|---|---|
| 1 | 1.05 : 1 | 4.2 – 4.4 | 5.8 | 0.15 | 89.5 | 205 |
| 2 | 1.05 : 1 | 4.2 – 4.4 | 6.6 | 0.15 | 90.5 | 220 |
| 3 | 1 : 1 | 4.2 – 4.4 | 6.5 | 0.17 | 79.0 | 203 |
| 4 | 1.1 : 1 | 4.2 – 4.4 | 6.2 | 0.14 | 77.5 | 185 |
| 5 | 105 : 1 | 6 – 7 | 6.7 | 0.18 | 72.2 | 195 |
| 6 | 105 : 1 | 3.5 | 5.6 | 0.16 | 78.6 | 160 |
| 7 | 1.05 : 1 | 4.2 – 4.4 | 9.6 | 0.25 | 82.9 | 209 |
| 8 | 1.05 : 1 | 4.2 – 4.4 | 3.0 | 0.08 | 56.6 | 70 |

We claim:

1. In a process for making acrylic acid by reacting acrolein with molecular oxygen in the presence of steam and, if desired, one or more inert gases, at elevated temperatures and in contact with a fixed bed cobalt molybdate catalyst, which has been prepared by precipitating cobalt molybdate from the combined aqueous solutions of a cobalt salt, of a molybdenum compound and of ammonia at a temperature of about 60°C and at a pH of at most 7; filtering off, washing and drying the resulting precipitate at a temperature of at least 100°C; heating the dry cobalt molybdate for several hours at elevated temperatures, grinding and transforming it into shapes and sintering the cobalt molybdate shapes for several hours, the improvement which comprises producing the acrylic acid in contact with a catalyst prepared by a process consisting essentially of combining an aqueous solution of the cobalt salt with that of the molybdenum compound in the atomic ratio of Co:Mo of about 1.05:1; establishing in the combined solutions a pH between 3.8 and 6.0; drying the precipitate at 110°–170°C; heating the dry cobalt molybdate over a period of 12 to 20 hours to temperatures between 250° and 550°C; and sintering the cobalt molybdate shapes over a period of 6 to 10 hours at temperatures between 500° and 700°C with the resultant formation of a cobalt molybdate catalyst having an inner surface area between 4 and 8 square meters/g and a volume of pores between 0.1 and 0.2 milliliters/g.

2. The process as claimed in claim 1, comprising using a catalyst prepared by combining an aqueous solution of cobalt nitrate with an aqueous ammoniacal solution of ammonium molybdate.

3. The process as claimed in claim 1, comprising using a catalyst prepared at a pH between 4.0 and 4.4.

4. The process as claimed in claim 1, comprising using a catalyst prepared by grinding cobalt molybdate and then compressing it into pellets with the use of about 2–5 weight % of graphite as a pelleting auxiliary.

5. The process as claimed in claim 1, comprising using a catalyst prepared by sintering the cobalt molybdate shapes and having an inner surface area between 5 and 7 square meters/g.

* * * * *

UNITED STATES PATENT AND TRADEMARK OFFICE
CERTIFICATE OF CORRECTION

PATENT NO. : 3,985,800
DATED : October 12, 1976
INVENTOR(S) : Heinz Erpenbach et al It is certified that error appears in the above—identified patent and that said Letters Patent are hereby corrected as shown below:

Column 3 lines 13 and 14 delete the parenthesis before "Mols" and after "converted", respectively.

Column 5, in the table, Example Nos. 5 and 6, second vertical column change "105 : 1" to --1.05 : 1--.

Signed and Sealed this

Twelfth Day of April 1977

[SEAL]

Attest:

RUTH C. MASON
*Attesting Officer*

C. MARSHALL DANN
*Commissioner of Patents and Trademarks*